United States Patent [19]

Talroze et al.

[11] 4,214,161
[45] Jul. 22, 1980

[54] APPARATUS FOR RADIOCHROMATOGRAPHIC ANALYSIS OF MIXTURE OF SUBSTANCES CONTAINING COMPONENTS TAGGED BY RADIOACTIVE ISOTOPES

[75] Inventors: Viktor L. Talroze; Vladimir D. Grishin; Boris A. Galushkin, all of Moscow, U.S.S.R.

[73] Assignee: Institut Khimicheskoi Fiziki Akademii Nauk USSR, U.S.S.R.

[21] Appl. No.: 867,154

[22] Filed: Jan. 5, 1978

[30] Foreign Application Priority Data

Jan. 24, 1977 [DE] Fed. Rep. of Germany ....... 2446411

[51] Int. Cl.² ............................................. G01T 1/161
[52] U.S. Cl. ..................................... 250/303; 73/231; 250/304; 250/328; 250/364
[58] Field of Search ................... 250/303, 304, 361 R, 250/364, 328; 73/23.1, 61.1 C; 210/31 C, 198 C; 23/232 C, 254 R

[56] References Cited

U.S. PATENT DOCUMENTS

| 3,590,247 | 6/1971 | Holford | 250/304 X |
| 3,883,739 | 5/1975 | Jenkins | 250/304 |

Primary Examiner—Davis L. Wallis
Attorney, Agent, or Firm—Steinberg and Blake

[57] ABSTRACT

Proposed is a device for radiochromatographic analysis of mixtures of substances containing components tagged by radioactive isotopes, such as soft β-isotopes comprising a chromatographic column, a detector of nuclear radiation and a chromatographic detector connected in series along the flow of the substance being analyzed. The detector of nuclear radiation is provided with a cell made as a tube with a scintillator applied onto its inner surface in the form of a solid layer. The tube is provided with movable means for sequentialy cooling and heating the same and a light detector which is movable along the length of the tube. In operation, upon introduction of the portion of the mixture being analyzed into the column, with the heater interacting with the tube, the heater and cooler are moved so that by the time the last component of the mixture exits from the column, the cooler is in interacting relationship with the tube whereby the components of the mixture are frozen. According to one mode of operation, the light detector is then moved to register the glow of the strips of the radioactive components whereby a radio-chromatogram can be derived.

4 Claims, 6 Drawing Figures

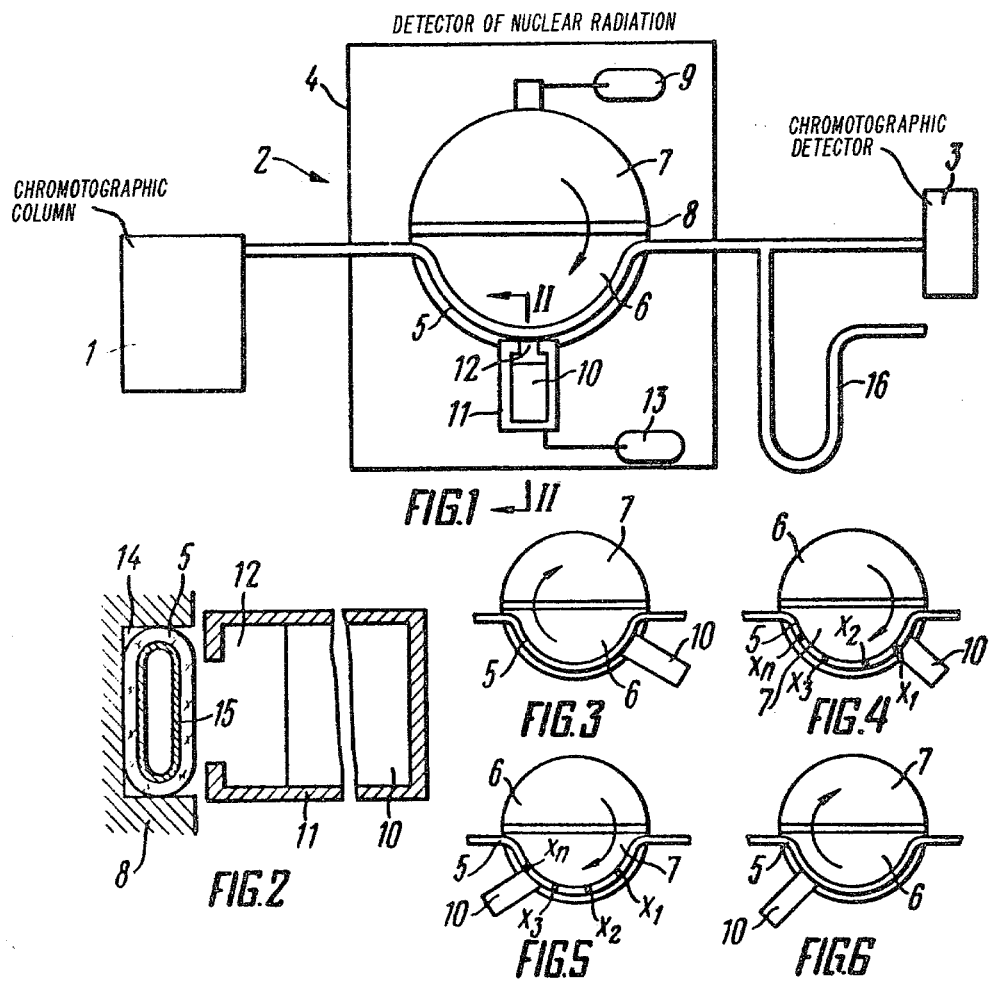

APPARATUS FOR RADIOCHROMATOGRAPHIC ANALYSIS OF MIXTURE OF SUBSTANCES CONTAINING COMPONENTS TAGGED BY RADIOACTIVE ISOTOPES

FIELD OF APPLICATION

The present invention relates to devices for investigating properties of substances by chromatographic analysis, and more particularly, to devices for chromatographic analysis, and more specifically, to devices for radiochromatographic analysis, and can be used most efficiently for measuring the radioactivity of chromatographically separated components of a mixture labelled with soft $\beta$-isotopes.

BACKGROUND OF THE INVENTION

Known in the art is a device for radiochromatographic analysis comprising a chromatographic column, a chromatographic detector and a detector of nuclear radiation made as a proportional flow counter. The disadvantages of such devices are the effect of the volume of the counter on chromatographic and radiochromatographic separation and the contamination of the counter with chromatographically separated components of the mixture (the so-called memory effects of the counter). In addition, to prevent the condensation of the components of the mixture the counter is usually heated to a temperature which is higher than the boiling point of the components. However, at high temperatures spurious pulses appear which result in a change of the Geiger plateau of the counter which affects its sensitivity.

The efficiency of the counter, and consequently, its sensitivity depend on the chemical properties of the components of the mixture because of their interaction with the gas filling the counter.

For the analysis of chromatographically separated radioactive components of the mixture there is known an all-purpose device comprising a chromatographic column, a detector of nuclear radiation and a chromatographic detector connected in series along the flow of the substance being investigated. In such a device the detector of nuclear radiation is made as a light-transparent cell filled with a liquid scintillator and a light detector optically connected therewith. The chromatographically separated radioactive components of the mixture being investigated are dissolved in the scintillator and continuously flow through the cell where the radioactivity of the components is measured by the light detector (*J. of Chromat.*, 1973, 76, 13).

In this device there is no necessity to heat the detector of nuclear radiation to high temperatures which makes it possible to investigate a wider range of substances, the volume of the detector does not affect chromatographic resolution, and there are no "memory effects".

However, the sensitivity of such device is limited by the residence time of the component in the throughflow cell. In addition, the sensitivity of the device is affected by quenching with scintillation, chemiluminescence, and limited solubility of the components being analyzed in the liquid scintillator characteristic of the given detector of nuclear radiation.

BRIEF DESCRIPTION OF THE INVENTION

It is a principal object of the invention to improve the sensitivity of the device for radiochromatographic analysis.

It is another object to eliminate the phenomena of quenching with scintillation and chemiluminescence in such device.

It is a third object of the invention to widen the range of the components of mixtures being analyzed.

These objects are attained by that in the device for radiochromatographic analysis of mixtures of substances containing components tagged by radioactive isotopes comprising a chromatographic column, a detector of nuclear radiation having a light-transparent cell with a scintillator, said cell being optically connected to a light detector, and a chromatographic detector, all connected in series along the flow of the substance being investigated, according to the invention, the cell is made as a tube, the scintillator is applied onto and overlies its inner surface as a solid layer, and the tube is provided with a cooler and a heater, the cooler, the heater and the light detector being movable along the tube.

To improve the process of freezing the component being investigated out of the flow of the carrier gas it is desirable to make the light-transparent tube with a substantially O-shaped cross section.

It is advisable that the cooler and the heater be disposed on opposed semi-circumferential edges of a disc rotatable about its axis, and the tube is formed so as to substantially conform to the shape of the semi-circumferential edge of the disc and disposed along its edge.

The device for radiochromatographic analysis made according to the present invention has a considerably higher sensitivity than the throughflow methods for measuring radioactivity of chromatographically separated components of the mixture labelled with soft $\beta$-isotopes. There is also no quenching with scintillation nor chemiluminesence, and no problem arises of solubility of the components being investigated in the liquid scintillator since the scintillator is applied onto a light-sensitive tube in the form of a solid layer.

BRIEF DESCRIPTION OF DRAWINGS

The invention is further explained by a description of its specific embodiments and by accompanying drawings wherein, according to the invention:

FIG. 1 shows a block diagram of a device for radiochromatographic analysis;

FIG. 2 is a section along II—II of FIG. 1;

FIGS. 3, 4, 5 and 6 show a detector of nuclear radiation at different stages of its operation.

DETAILED DESCRIPTION OF THE INVENTION

The propesed device for radiochromatographic analysis comprises a chromatographic column 1 (FIG. 1), a detector 2 of nuclear radiation and a chromatographic detector 3 connected in series along the flow of the substance being investigated.

The detector 2 of nuclear radiation comprises a light-transparent cell in the form of a tube 5 disposed in an opaque housing, as well as a heater 6 and a cooler 7 mounted on the opposed semi-circumferential edge portions of a disc 8 made of a heat-insulating material. The disc 8 is provided with a drive, schematically illustrated at 9, which rotates the disc 8 about its axis passing through its center. The detector 2 of nuclear radiation also comprises a light detector 10 (photoelectron multiplier) placed in its opaque housing 11 with a collimation diaphragm 12 facing the tube 5 and ensuring optical connection of the light detector 10 with the tube 5. The light detector 10 has an electric drive, schematically illustrated at 13, for movement of the detector 10 along the length of the tube 5. The tube 5 itself is formed so as to conform to the shape of the semi-circumferential edge portions of the disc 8 and is placed along its edge in a slot 14 specially provided for this purpose (FIG. 2). It is also seen in FIG. 2 that the tube 5 has a substantially O-shaped cross section and a scintillator 15 is applied onto and overlies its inner surface in the form of a solid layer. A trap 16 is mounted at the outlet of the detector 2 (FIG. 1) of nuclear radiation for collecting the mixture components which have been investigated.

FIGS. 3, 4, 5 and 6 are intended for illustrating the operation of the device and will be explained below.

The device operates in the following manner.

Prior to the beginning of operation the heater 6, the cooler 7 and the light detector 10 are arranged as shown in FIG. 3. The disc 8 is in such a position in which the heater 6 mounted on a semi-circumferential edge portion of disc 8 interacts with the tube 5. The light detector 10 is disposed at the outlet of the tube 5. Immediately after the introduction into the chromatographic column 1 of a portion of the mixture being analyzed consisting of the components tagged by isotopes $x_1$, $x_2$. . . $x_n$ (or with a time delay equal, for example, to the duration of the movement through the column of the carrier gas or the first component of the mixture) the heater 6 and the cooler 7 which is mounted on the opposed semi-circumferential edge portions of disc 8 are rotated by the electric drive 9 to meet the flow of the carrier gas. The speed of movement of the heater 6 and the cooler 7 is selected so that by the moment of egress from the chromatographic column 1 of the last component $x_n$ of the mixture the heater 6 and the cooler 7 have rotated by about 180°, as shown in FIG. 4, i.e. so that the cooler 7 interacts with the tube 5. In this case the entire length of the tube 5 is used for freezing the radioactive components $x_1$, $x_2$. . . $x_n$ within the tube 5. As a result of a sharp temperature jump in the tube 5 at the border between the heater 6 and the cooler 7 during their movement along the tube 5 all the mixture components are frozen in the form of short strips, in the place where this border meets the component passing through the tube 5. During the freezing of the components $x_1$, $x_2$. . . $x_n$ of the mixture the light detector 10 is in a position close to the outlet of the tube 5 along the flow of the components $x_1$, $x_2$. . . $x_n$ being investigated. When the heater 6 and the cooler 7 end their movement the electric drive 13 is actuated which puts in motion the light detector 10 to meet the flow of the carrier gas, the light detector 10 registering the glow of strips of radioactive components $x_1$, $x_2$. . . $x_n$, i.e. a radiochromatogram of the mixture is derived. In other words, the strips of radioactive components $x_1$, $x_2$, . . . $x_n$, which are frozen in the tube 5 as described above comprise sources of radiation which emit $\beta$ particles which cause a luminescence of the scintillator 15 which is recorded by light detector 10. In this manner, the radioactivity of the separated components of the mixture is estimated or, in other words, a radiochromatographic analysis is carried out. Each frozen strip comprises a different component of the mixture. The components of the mixture are frozen in the form of short strips separated from each other by a distance determined by the time interval between successive components exiting from the chromatographic column. In this manner, the speed of movement of the heater and cooler 6, 7 is determined. The light detector 10 can move many times both against the flow of the carrier gas and back registering radiochromatograms as many times as necessary. After a radiochromatogram has been registered the light detector 10 is disposed near the inlet of the tube 5 as is shown in FIG. 5. The light detector 10 can also be disposed opposite a strip of any frozen-out radioactive component, the size of the diaphragm 12 of the light detector 10 being made greater than the width of the frozen strip, and the light detector 10 measuring the radioactivity of the chosen component. Thus, the registration of the radioactivity of the components $x_1$, $x_2$. . . $x_n$ can be accomplished by two methods: a differential method wherein the light detector 10 continuously moves at a pre-selected speed along the tube 5 registering the radiochromatogram of the mixture of radioactive components $x_1$, $x_2$. . . $x_n$, and/or an integral method wherein the light detector 10 is positioned opposite a strip of the frozen-out component and for a pre-selected interval registers the radioactivity of the component being analyzed. The integral method of registration makes it possible to considerably improve the sensitivity of the device since the sensitivity in such measurements is proportional to $\sqrt{T}$ where T is the time of measurement which in this case is unlimited. The device makes it possible to use the sample for analysis many times. For this purpose, after all the required measurements of radioactivity have been made, the electric drive 9 is actuated and the border between the heater 6 and the cooler 7 begins to move along the tube 5 defrosting the components $x_1$, $x_2$. . . $x_n$ frozen out in the tube 5. The movement is continued until the tube 5 is fully in the zone of the heater 6 as shown in FIG. 6, the entire mixture or the selected components thereof after the analysis being collected in the trap 16 (FIG. 1) disposed at the outlet of the device.

Thus, the mixture comprising components tagged by soft $\beta$-isotopes is introduced into the chromatographic column, where it is divided into independent components which, upon exiting from the chromatographic column, are subsequently supplied to a light-transparent tube, an internal surface of which is coated by a scintillator. A heater and cooler fastened on opposed peripheral semi-circumferential edge portions of a disc are moved along the tube countercurrently to gas-carrier flow resulting in the creation of a temperature drop in the tube. Each individual component of the mixture, while being in the zone of the cooler, is frozen and condensed in the form of a narrow strip on the scintillator coated internal wall of the tube on the spot where the temperature drop occurs. The other components of the mixture being investigated are also similarly condensed on the scintillator coated internal wall of the tube as they exit from the chromatographic column in the form of narrow strips spaced along the length of the tube, due to movement of the cooler along the length of the tube. In this case, a scintillator luminescence occurs in the place of location of the components tagged by the $\beta$-isotope and which is recorded by the light detector (comprising a photoelectron multiplier) disposed inside the tube. Thus, the component tagged by $\beta$-isotope is a radioactive radiation source. After recording the radioactivity of the tagged components, the latter are heated and defrosted and supplied to the chromatographic detector which records the chromatographic chart of the mixture.

The proposed device can be used with any type of the chromatographic detector 3 in combination with chromate mass spectral and chromate effusion mass spectrometric devices and can effect the concentration of the components of the mixture being analyzed.

What is claimed is:

1. A device for radiochromatographic analysis of mixtures of substances containing components tagged by radioactive isotopes comprising: a chromatographic column; a detector of nuclear radiation connected in series with the outlet of said chromatographic column along the flow of the substance being analyzed; a chromatographic detector connected in series with the outlet of said detector of nuclear radiation along the flow of the substance being analyzed; said nuclear radiation detector including a tubular shaped light-transparent cell, one end of said tube being in fluid communication with said chromatographic column and comprising the inlet of said detector of nuclear radiation, the other end of said tube being in fluid communication with said chromatographic detector and comprising the outlet of said detector of nuclear radiation; a scintillator constituting a solid layer overlying the inner surface of said tube; a heater movable along the length of said tube; a cooler movable along the length of said tube consecutively with said heater; means for moving said heater and cooler consecutively along the length of said tube; a light detector optically connected to said tube and movable therealong; and means for moving said light detector along said tube.

2. A device as claimed in claim 1, wherein said tube has a substantially O-shaped cross section.

3. A device as claimed in claim 2 comprising a disc mounted for rotation about an axis; said heater and cooler being mounted on the opposed semi-circumferences of said disc; said tube being formed substantially in the shape of the semi-circumference of said disc and disposed along its edge.

4. A device as claimed in claim 1, comprising a disc mounted for rotation about an axis; said heater and cooler being mounted on opposed semi-circumferences of said disc; said tube being formed substantially in the semi-circumference of said disc and disposed along its edge.

* * * * *